(12) United States Patent
Cuthbertson et al.

(10) Patent No.: US 7,608,243 B2
(45) Date of Patent: Oct. 27, 2009

(54) FLUORESCEIN-LABELLED PEPTIDES

(75) Inventors: Alan Cuthbertson, Oslo (NO); Bard Indrevoll, Oslo (NO); Magne Solbakken, Oslo (NO)

(73) Assignee: GE Healthcare AS, Oslo (NO)

( * ) Notice: Subject to any disclaimer, the term of this patent is extended or adjusted under 35 U.S.C. 154(b) by 656 days.

(21) Appl. No.: 10/560,062

(22) PCT Filed: Jul. 7, 2004

(86) PCT No.: PCT/NO2004/000208

§ 371 (c)(1),
(2), (4) Date: Dec. 8, 2005

(87) PCT Pub. No.: WO2005/003166

PCT Pub. Date: Jan. 13, 2005

(65) Prior Publication Data

US 2007/0183977 A1    Aug. 9, 2007

(30) Foreign Application Priority Data

Jul. 8, 2003    (NO) .................................. 20033115

(51) Int. Cl.
*A61K 51/00*    (2006.01)
*A61M 36/14*    (2006.01)

(52) U.S. Cl. .................... 424/1.69; 424/1.11; 424/1.65; 424/9.6

(58) Field of Classification Search ................ 424/1.11, 424/1.65, 1.69, 1.81, 1.85, 1.89, 9.1, 9.3, 424/9.4, 9.5, 9.6, 9.7; 530/300
See application file for complete search history.

(56) References Cited

U.S. PATENT DOCUMENTS 7,351,790 B2 * 4/2008 Cuthbertson et al. ........ 530/317
7,368,474 B2 * 5/2008 Cuthbertson et al. ........ 514/453
7,410,943 B2 * 8/2008 Cuthbertson et al. ........... 514/2
7,521,419 B2 * 4/2009 Cuthbertson et al. .......... 514/10
2002/0102217 A1    8/2002 Hellebust et al.

FOREIGN PATENT DOCUMENTS

WO        01/77145       10/2001
WO        02/26776        4/2002

OTHER PUBLICATIONS

Katada, et.al., "A Novel Motif for Platelet Fibrinogen Receptor Recognition" The Journal of Biological Chemistry, vol. 272, No. 12, Mar. 21, 1997, pp. 7720-7726.
Reicke, B., et.al. "Topical Application of Integrin Antagonists Inhibits Proliferative Retinopathy" Hormone and Metabolic Research, vol. 33, No. 5, May 2001, pp. 307-311.
De Groot F.M.H., et.al., "Design, Synthesis, and Biological Evaluation of a Dual Tumor-Specific Motive Containing Integrin-Targeted Plasmin-Cleavable Doxorubicin Prodrug" Molecular Cancer Therapeutics, American Assoc. of Cancer Research, US, vol. 1, Sept. 2002, pp. 901-911.
Int'l Search Report PCT/NO2004/000208 dated Dec. 2004.
Int'l Preliminary Exam report PCT/NO2004/000208 dated Sep. 2005.

* cited by examiner

*Primary Examiner*—D L Jones
(74) *Attorney, Agent, or Firm*—Craig Bohlken

(57) ABSTRACT

The invention relates to new peptide-based compounds and their use in diagnostic optical imaging. More specifically the invention relates to the use of such peptide-based compounds as targeting vectors that bind to receptors associated with angiogenesis. The compounds are labeled with fluorescein and may be used as contrast agents in optical imaging in diagnosis of angiogenesis-related diseases.

10 Claims, No Drawings

SEQUENCE LISTING

```
<160> NUMBER OF SEQ ID NOS: 8

<210> SEQ ID NO 1
<211> LENGTH: 8
<212> TYPE: PRT
<213> ORGANISM: Artificial sequence
<220> FEATURE:
<223> OTHER INFORMATION: Synthesised peptide

<400> SEQUENCE: 1

Lys Cys Arg Gly Asp Cys Phe Cys
1               5

<210> SEQ ID NO 2
<211> LENGTH: 8
<212> TYPE: PRT
<213> ORGANISM: Artificial sequence
<220> FEATURE:
<223> OTHER INFORMATION: Synthesised peptide
<220> FEATURE:
<221> NAME/KEY: THIOETH
<222> LOCATION: (1)..(8)
<223> OTHER INFORMATION: Thioether  bridge between amino acids 1 and 8.
<220> FEATURE:
<221> NAME/KEY: DISULFID
<222> LOCATION: (2)..(6)
<223> OTHER INFORMATION: Disulphide bridge between amino acids 2 and 6.

<400> SEQUENCE: 2

Lys Cys Arg Gly Asp Cys Phe Cys
1               5

<210> SEQ ID NO 3
<211> LENGTH: 10
<212> TYPE: PRT
<213> ORGANISM: Artificial sequence
<220> FEATURE:
<223> OTHER INFORMATION: Synthesised peptide

<400> SEQUENCE: 3

Lys Asp Cys Arg Gly Asp Cys Phe Cys Gly
1               5                   10

<210> SEQ ID NO 4
<211> LENGTH: 10
<212> TYPE: PRT
<213> ORGANISM: Artificial sequence
<220> FEATURE:
<223> OTHER INFORMATION: Synthesised peptide
<220> FEATURE:
<221> NAME/KEY: THIOETH
<222> LOCATION: (1)..(3)
<223> OTHER INFORMATION: Thioether bridge between amino acids 1 and 3
<220> FEATURE:
<221> NAME/KEY: DISULFID
<222> LOCATION: (7)..(9)
<223> OTHER INFORMATION: Disulphide bridge between amino acids 7 and 9

<400> SEQUENCE: 4

Lys Asp Cys Arg Gly Asp Cys Phe Cys Gly
1               5                   10

<210> SEQ ID NO 5
<211> LENGTH: 8
```

```
-continued

<212> TYPE: PRT
<213> ORGANISM: Artificial sequence
<220> FEATURE:
<223> OTHER INFORMATION: Synthesised peptide

<400> SEQUENCE: 5

Lys Cys Arg Gly Asp Cys Phe Cys
1               5

<210> SEQ ID NO 6
<211> LENGTH: 8
<212> TYPE: PRT
<213> ORGANISM: Artificial sequence
<220> FEATURE:
<223> OTHER INFORMATION: Synthesised peptide
<220> FEATURE:
<221> NAME/KEY: THIOETH
<222> LOCATION: (1)..(6)
<223> OTHER INFORMATION: Thioether bridge between amino acids 1 and 6
<220> FEATURE:
<221> NAME/KEY: DISULFID
<222> LOCATION: (2)..(8)
<223> OTHER INFORMATION: Disulphide bridge between amino acids 2 and 8.

<400> SEQUENCE: 6

Lys Cys Arg Gly Asp Cys Phe Cys
1               5

<210> SEQ ID NO 7
<211> LENGTH: 8
<212> TYPE: PRT
<213> ORGANISM: Artificial sequence
<220> FEATURE:
<223> OTHER INFORMATION: Synthesised peptide

<400> SEQUENCE: 7

Asp Cys Arg Gly Asp Cys Phe Cys
1               5

<210> SEQ ID NO 8
<211> LENGTH: 8
<212> TYPE: PRT
<213> ORGANISM: Artificial sequence
<220> FEATURE:
<223> OTHER INFORMATION: Synthesised peptide
<220> FEATURE:
<221> NAME/KEY: THIOETH
<222> LOCATION: (1)..(8)
<223> OTHER INFORMATION: Thioether bridge between amino acids 1 and 8
<220> FEATURE:
<221> NAME/KEY: DISULFID
<222> LOCATION: (2)..(6)
<223> OTHER INFORMATION: Disulphide bridge between amino aids 2 and 6

<400> SEQUENCE: 8

Asp Cys Arg Gly Asp Cys Phe Cys
1               5
```

FLUORESCEIN-LABELLED PEPTIDES

This application is a filing under 35 U.S.C. 371 of international application No. PCT/NO2004/000208, filed Jul. 7, 2004, which claims priority to application No. 20033115 filed Jul. 8, 2003, in Norway the entire disclosure of which is hereby incorporated by reference.

FIELD OF THE INVENTION

This invention relates to new peptide-based compounds and their use in diagnostic optical imaging or for the treatment of disease. More specifically the invention relates to the use of such peptide-based compounds as targeting vectors that bind to receptors associated with angiogenesis. The compounds may be used as contrast agents in diagnosis of angiogenesis-related diseases.

BACKGROUND OF INVENTION

Generally, new blood vessels can be formed by two different mechanisms: vasculogenesis or angiogenesis. Angiogenesis is the formation of new blood vessels by branching from existing vessels. The primary stimulus for this process may be inadequate supply of nutrients and oxygen (hypoxia) to cells in a tissue. The cells may respond by secreting angiogenic factors, of which there are many; one example, which is frequently referred to, is vascular endothelial growth factor (VEGF). These factors initiate the secretion of proteolytic enzymes that break down the proteins of the basement membrane, as well as inhibitors that limit the action of these potentially harmful enzymes. The other prominent effect of angiogenic factors is to cause endothelial cells to migrate and divide. Endothelial cells that are attached to the basement membrane, which forms a continuous sheet around blood vessels on the contralumenal side, do not undergo mitosis. The combined effect of loss of attachment and signals from the receptors for angiogenic factors is to cause the endothelial cells to move, multiply, and rearrange themselves, and finally to synthesise a basement membrane around the new vessels.

Angiogenesis is prominent in the growth and remodelling of tissues, including wound healing and inflammatory processes. Inhibition of angiogenesis is also considered to be a promising strategy for antitumour therapy. The transformations accompanying angiogenesis are also very promising for diagnosis, an obvious example being malignant disease, but the concept also shows great promise in inflammation and a variety of inflammation-related diseases, including atherosclerosis, the macrophages of early atherosclerotic lesions being potential sources of angiogenic factors. These factors are also involved in re-vascularisation of infarcted parts of the myocardium, which occurs if a stenosis is released within a short time.

Further examples of undesired conditions that are associated with neovascularization or angiogenesis, the development or proliferation of new blood vessels are shown below. Reference is also made in this regard to WO 98/47541.

Diseases and indications associated with angiogenesis are e.g. different forms of cancer and metastasis, e.g. breast, skin, colorectal, pancreatic, prostate, lung or ovarian cancer.

Other diseases and indications are inflammation (e.g. chronic), atherosclerosis, rheumatoid arthritis and gingivitis.

Further diseases and indications associated with angiogenesis are arteriovenous malformations, astrocytomas, choriocarcinomas, glioblastomas, gliomas, hemangiomas (childhood, capillary), hepatomas, hyperplastic endometrium, ischemic myocardium, endometriosis, Kaposi sarcoma, melanoma, neuroblastomas, occluding peripheral artery disease, osteoarthritis, psoriasis, retinopathy (diabetic, proliferative), scleroderma, seminomas and ulcerative colitis.

Angiogenesis involves receptors that are unique to endothelial cells and surrounding tissues. These markers include growth factor receptors such as VEGF and the Integrin family of receptors. Immunohistochemical studies have demonstrated that a variety of integrins, perhaps most importantly the $\alpha_v$ class, are expressed on the apical surface of blood vessels [Conforti, G., et al. (1992) Blood 80: 37-446] and are available for targeting by circulating ligands [Pasqualini, R., et al. (1997) Nature Biotechnology 15: 542-546]. The $\alpha5\beta1$ is also an important integrin in promoting the assembly of fibronectin matrix and initiating cell attachment to fibronectin. It also plays a crucial role in cell migration.

The integrin $\alpha v \beta 3$ is one of the receptors that is known to be associated with angiogenesis. Stimulated endothelial cells appear to rely on this receptor for survival during a critical period of the angiogeneic process, as antagonists of the $\alpha v \beta 3$ integrin receptor/ligand interaction induce apoptosis and inhibit blood vessel growth.

Integrins are heterodimeric molecules in which the $\alpha$- and $\beta$-subunits penetrate the cell-membrane lipid bilayer. The $\alpha$-subunit has four $Ca^{2+}$ binding domains on its extracellular chain, and the $\beta$-subunit has a number of extracellular cysteine-rich domains.

Many ligands (eg. fibronectin) involved in cell adhesion contain the tripeptide sequence arginine-glycine-aspartic acid (RGD). The RGD sequence appears to act as a primary recognition site between the ligands presenting this sequence and receptors on the surface of cells. It is generally believed that secondary interactions between the ligand and receptor enhance the specificity of the interaction. These secondary interactions might take place between moieties of the ligand and receptor that are immediately adjacent to the RGD sequence or at sites that are distant from the RGD sequence.

RGD peptides are known to bind to a range of integrin receptors and have the potential to regulate a number of cellular events of significant application in the clinical setting. Perhaps the most widely studied effect of RGD peptides and mimetics thereof relate to their use as anti-thrombotic agents where they target the platelet integrin GpIIbIIIa.

Inhibition of angiogenesis in tissues by administration of either an $\alpha v \beta 3$ or $\alpha v \beta 5$ antagonist has been described in for example WO 97/06791 and WO 95/25543 using either antibodies or RGD containing peptides. EP 578083 describes a series of mono-cyclic RGD containing peptides.

Cyclic RGD peptides containing multiple bridges have also been described in WO 98/54347 and WO 95/14714.

Further examples of RGD comprising peptide-based compounds are found in WO01/77145, WO02/26776 and WO03/006491.

There is a clinical need to develop more specific non-invasive imaging techniques for angiogenesis-related diseases. Such imaging techniques will have a central role in the evaluation of novel anti-angiogenic therapies. Being able to assess the actual level of angiogenesis will be of clinical benefit in diagnosing angiogenesis-related diseases at an early stage. It has now surprisingly been found that optical imaging may be used to assess the level of angiogenesis, and the invention provides new optical imaging contrast agents for this purpose.

SUMMARY OF THE INVENTION

In view of the needs of the art the present invention provides peptide-based compounds labeled with fluorescein for use as contrast agents in optical imaging or for therapeutic treatment. The efficient targeting and imaging of integrin receptors associated with angiogenesis in vivo demands a selective, high affinity RGD based vector that is chemically robust and stable. Furthermore, the route of excretion is an important factor when designing imaging agents in order to reduce problems with background noise. These stringent conditions are met by the fluorescein-labelled peptide compounds described in the present invention.

DETAILED DESCRIPTION OF THE INVENTION

Viewed from one aspect the invention provides new peptide-based compounds as defined in the claims. These compounds have affinity for integrin receptors, e.g. affinity for the integrin αvβ3, and are labeled with a fluorescein dye reporter.

The compounds, or physiologically acceptable salts thereof, comprise a peptidic vector and at least one fluorescein dye, wherein the peptidic vector comprises the amino acid sequence $X_3$-G-D and wherein the peptidic vector and the fluorescein dyes are coupled, preferably by covalent bonds. $X_3$ represents arginine, N-methylarginine or an arginine mimetic, G represents glycine and D represents aspartic acid. The peptidic vector has affinity for integrin receptors, such as the αvβ3 receptors.

The compounds of the invention comprise the amino acid sequence $X_3$-G-D having affinity for the integrin receptors. The compound preferably comprises further amino acids, and optional other moieties, wherein the $X_3$-G-D sequence is the binding seat of the peptidic vector which function as a vector binding to an integrin type receptor.

The compound of the invention can be constrained for example by formation of one or more cyclising bridges in the peptidic vector part. A monocyclic peptide compound can be obtained by formation of a disulfide bond or a thioether bond between amino acids. A peptide-based compound including one cyclising bridge is more specific towards αvβ3, and is more preferred, than a linear peptide. The compounds of the invention preferably comprise two cyclising bridges between different amino acids of the compounds. The term "cyclising bridges" refers to any combination of amino acids or with amino acids and —$(CH_2)n$— or —$(CH_2)n$—$C_6H_4$— groups with functional groups which allows for the introduction of a bridge. n represents a positive integer from 1 to 10. Some preferred examples are disulphides, disulphide mimetics such as the —$(CH_2)_4$— carba bridge, thioacetal, thioether bridges (cystathione or lanthionine) and bridges containing esters and ethers. Preferably, one bridge forms a disulphide bond and a second bridge comprises a thioether (sulphide) bond.

In a further embodiment the compounds of the invention are identified by formula (I)

$$R_a-C(=O)-X_1-X_2-X_3-G-D-X_4-X_5-X_6-X_7 \quad (I)$$

comprising two cyclising bridges, wherein, $X_3$, G and D are as previously defined; and $R_a$ represents —$(CH_2)_n$— or —$(CH_2)_n$—$C_6H_4$— forming a bridge to either of $X_2$, $X_4$ or $X_6$, wherein n represents a positive integer from 1 to 10; and $X_1$ represents a-bond or 1, 2, 3, 4 or 5 amino acid residues, wherein one amino acid residue is optionally functionalised with a spacer moiety, and preferably said amino acid residue possesses a functional side-chain such as an acid or amine group preferably selected from aspartic or glutamic acid, lysine, homolysine, diaminoalcylic acid or diaminopropionic acid; and $X_2$ and $X_4$ represent independently amino acids residues capable of forming a cyclising bridge, such as cysteine or homocysteine residues forming disulphide or thioether bonds, or other amino acid residues capable of forming a cyclising bridge such as aspartic acid and lysine, preferably $X_2$ and $X_4$ represent residues of cysteine or homocysteine; and $X_5$ represents a hydrophobic amino acid or derivatives thereof, and preferably represents a tyrosine, a phenylalanine, a 3-iodo-tyrosine or a naphthylalanine residue, and more preferably a phenylalanine or a 3-iodo-tyrosine residue; and $X_6$ represents an amino acid residue capable of forming a cyclising bridge, preferably a thiol-containing amino-acid residue, preferably a cysteine or a homocysteine residue; and $X_7$ represents a spacer or biomodifier moiety or is absent, and is preferably based on a monodisperse polyethylene glycol (PEG) building block comprising 1 to 10 units of said building block, said biomodifier having the function of modifying the pharmacokinetics and blood clearance rates of said agents. In addition $X_7$ may also represent 1 to 10 amino acid residues preferably comprising glycine, lysine, aspartic acid or serine. More preferably, $X_7$ represent a spacer or biomodifier comprising both amino acid residues and a PEG-like structure, such as 1-10 amino acid residues in combination with a PEG-like structure, preferably a bis aminoethyl ethylene glycol glycine combination. In a preferred embodiment $X_7$ represents a unit comprised of the monodisperse PEG-like structure, 17-amino-5-oxo-6-aza-3, 9, 12, 15-tetraoxaheptadecanoic acid of formula (II),

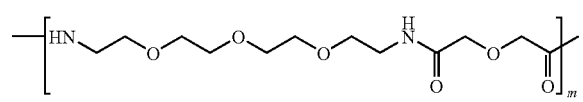

wherein m equals an integer from 1 to 10 and where the C-terminal end is an amide or acid moiety. It is found that the biomodifier, $X_7$, modifies the pharmacokinetics and blood clearance rates of the compounds. The biomodifier effects less uptake of the compounds in tissue i.e. muscle, liver etc. thus giving a better diagnostic image due to less background interference. The secretion is mainly through the kidneys due to a further advantage of the biomodifier; and the compound further comprising at least one group Z, representing a fluorescein group, linked to one or more of $X_1$, $X_6$ or $X_7$, optionally via a spacer group.

The peptide-based compound comprises a peptidic vector defined by the amino sequence formed by $X_1$, $X_2$, $X_3$, G, D, $X_4$, $X_5$ and $X_6$ of Formula I and this peptide constitute a targeting vector having affinity for integrin receptors associated with angiogenesis.

Depending of the placement of the cyclising bridges the compounds will comprise "discrete", "nested" or "interlocking" configurations. Preferably the two bridges in each compounds are:

Between $R_a$ and $X_6$, and between $X_2$ and $X_4$ (forming a nested configuration);

Between $R_a$ and $X_2$, and $X_4$ and $X_6$ (discrete configuration);

Between $R_a$ and $X_4$, and $X_2$ and $X_6$ (forming an interlocking configuration).

In a further embodiment the compounds of the invention are identified by either of the formulas below:

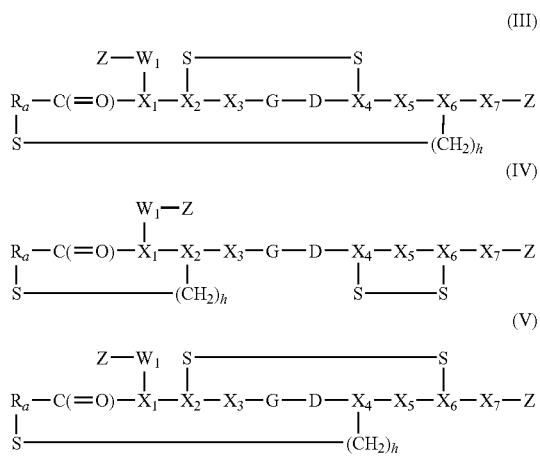

wherein $R_a$, $X_1$, $X_3$, G, D, $X_5$, and $X_7$ are as defined for formula I; and wherein $X_2$, $X^4$ and $X_6$ represent amino acid residues capable of forming a disulphide or a thioether bond, such as cysteines or homocysteines;

$W_1$ is a spacer moiety or is absent, and is preferentially derived from glutaric and/or succinic acid and/or a polyethylenglycol based unit, e.g. including a moiety as given for formula II, linking the fluorescein dye to the peptide. Other representative spacer ($W_1$) elements include structural-type polysaccharides, storage-type polysaccharides, polyamino acids and methyl and ethyl esters thereof, and polypeptides, oligosaccharides and oligonucleotides, which may or may not contain enzyme cleavage sites. The role of the spacer moiety $W_1$ is to distance the relatively bulky dye from the receptor binding domain of the peptide component;

h is a positive integer 1 or 2;

and wherein at least one of the Z groups is present representing a fluorescein dye.

The compounds preferably include only one Z-group.

The fluorescein dye, represented by Z may be linked to $X_1$, $W_1$, $X_6$ or $X_7$, preferably by amide bond formation.

In a preferred aspect the compounds of formula III-V, or the physiologically acceptable salts thereof, have the following characteristics:

$R_a$ preferably represents —(CH$_2$)—.

Further, $X_1$ represents an amino acid residue with a functional side-chain such as an acid or amine group, the amino acid preferably being selected from aspartic or glutamic acid, lysine, homolysine, diaminoalcylic acid or diaminopropionic acid, more preferably aspartic acid or lysine.

$X_2$, $X_4$ and $X_6$ preferably independently represent a cysteine or a homocysteine residue.

$X_3$ preferably represents arginine.

$X_5$ preferably represents tyrosine, phenylalanine, 3-iodo-tyrosine or naphthylalanine, and more preferably phenylalanine or 3-iodo-tyrosine.

$X_7$ and $W_1$ are defined as for formula I and II-V respectively. Preferably $X_7$ comprises 1-10 units of a monodisperse PEG building block or is absent, and $W_1$ is preferably absent.

Z represents a fluorescein dye or is absent, such that the compound comprises at least one fluorescein dye.

In a preferred aspect the compounds are of formula III (nested) or physiologically acceptable salts thereof, and more preferably they have the characteristics given in the preferred aspect described above.

The compounds of formula III-V comprise at least two bridges, wherein one bridge forms a disulphide bond and the second bridge comprises a thioether (sulphide) bond. The preferred compounds, of formula III, have the bridges placed such the bridges fold the peptide moiety into a 'nested' configuration. The compounds of this embodiment of the invention thus have a maximum of one disulphide bridge per molecule moiety. Compounds defined by the present invention are surprisingly stable in vivo and under the conditions employed during labeling with fluorescein.

The reporter Z comprises a fluorescein dye, i.e. fluorescein or derivatives of fluorescein. Fluorescein is a yellow dye which glows in visible light. Fluorescein is typically excited by the 488 nm line of an argon laser, and emission is collected at 530 nm. Fluorescein and its derivatives have relatively high absorptivity, excellent fluorescence quantum yield and good water solubility. The extensive use in the past makes them very well characterised, the availability is very good and they have a general low cost per mg.

Formula (VI) gives fluorescein, showing the numbering of the different positions.

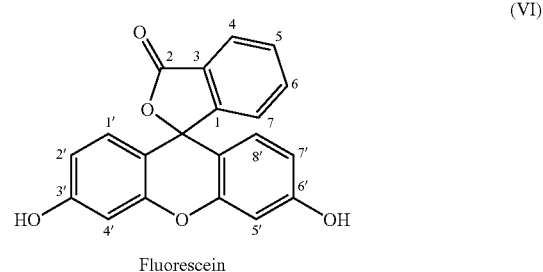

Fluorescein

Relevant derivatives of fluorescein are e.g. the carboxyfluoresceins, such as the 5-carboxyfluorescein, shown by formula VII, or the 6-carboxyfluorescein.

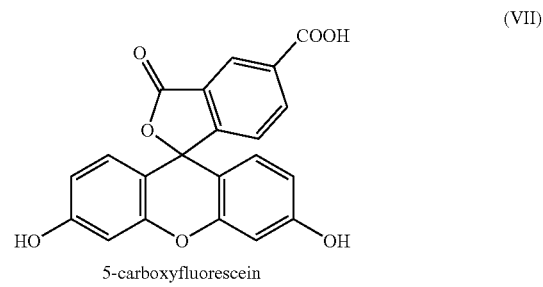

5-carboxyfluorescein

Another relevant fluorescein derivative is fluorescein isothiocyanate given by formula VIII:

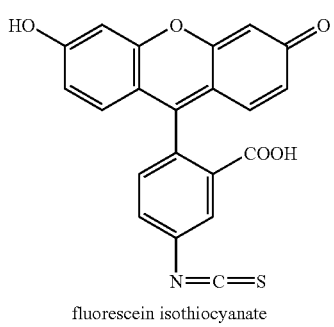

fluorescein isothiocyanate (VIII)

Even more preferred is to use an activated carboxylate of fluorescein, such as an N-hydroxysuccinimide (NHS) ester, called fluorescein NHS ester, shown in formula IX. Succinimidyl esters are excellent reagents since the amide products formed are very stable.

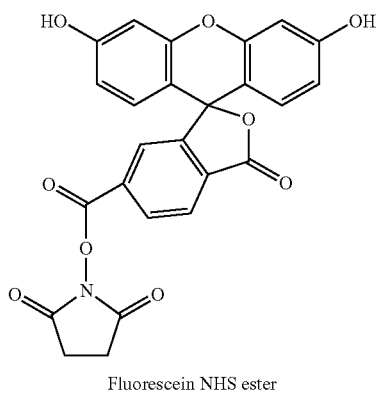

Fluorescein NHS ester (IX)

The fluorescein dye, represented by Z, may be linked to $X_1$, $X_6$ or $X_7$ of formula I, or optionally via the spacer $W_1$ as given in formulas III-V. Preferably, fluorescein is coupled to the peptidic vector by amide bond formation with a suitable amino group of the peptide. Active esters of fluorescein such as the NHS ester (Pierce Catalog 46100) are considered particularly useful when synthesising the compounds. Preferred coupling sites for the fluorescein are position 5 and 6.

The amino acids may preferably represent a naturally occurring amino acid. In most cases, it is preferred that the amino acids in the peptide are all in the L-form. However, in some embodiments of the invention one, two, three or more of the amino acids in the peptide are preferably in the D-form. The inclusion of such D-form amino acids can have a significant effect on the serum stability of the compound.

Some of the compounds of the invention are high affinity RGD based vectors. As used herein the term 'high affinity RGD based vector' refers to compounds that have a Ki of <10 nM and preferably <5 nM, in a competitive binding assay for αvβ3 integrin and where the Ki value was determined by competition with the known high affinity ligand echistatin. Methods for carrying out such competition assays are well known in the art.

Some preferred compounds of the invention are illustrated below. Compounds A and B comprise fluorescein conjugated to an RGD-containing peptide (Lys-Cys-Arg-Gly-Asp-Cys-Phe-Cys by amide bond formation, both giving a "nested" configuration.

Compound A:

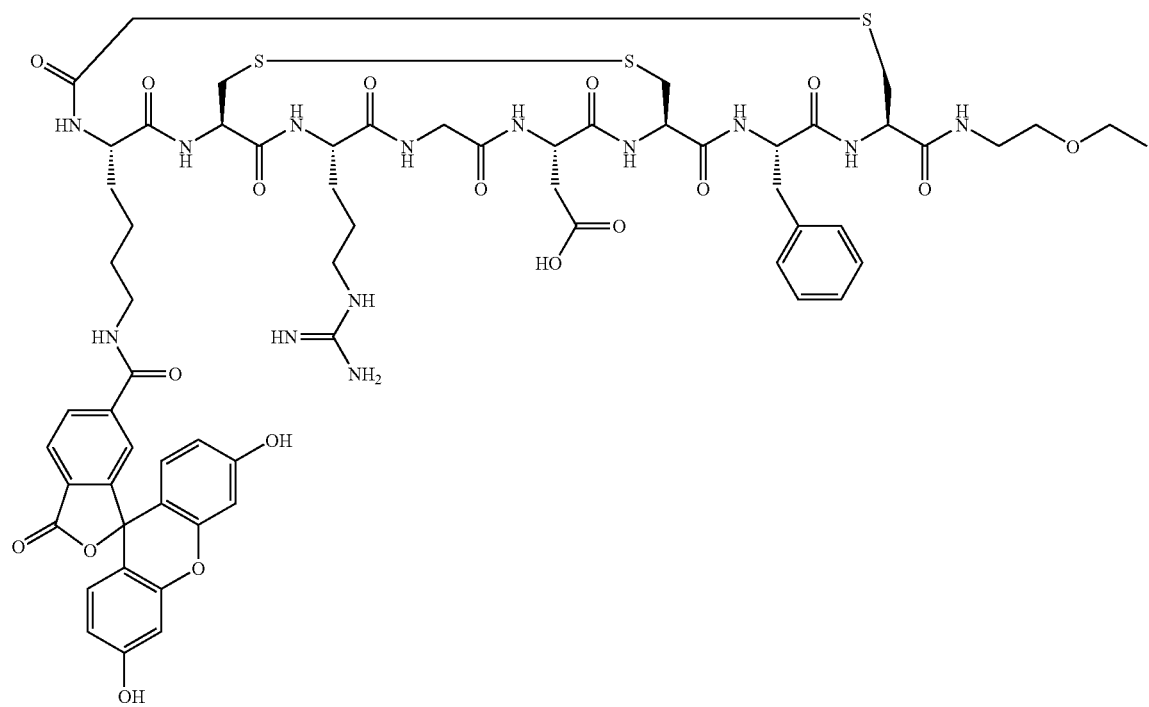

-continued

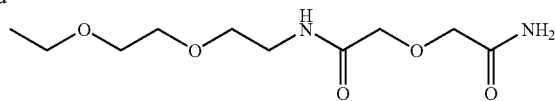

Compound B:

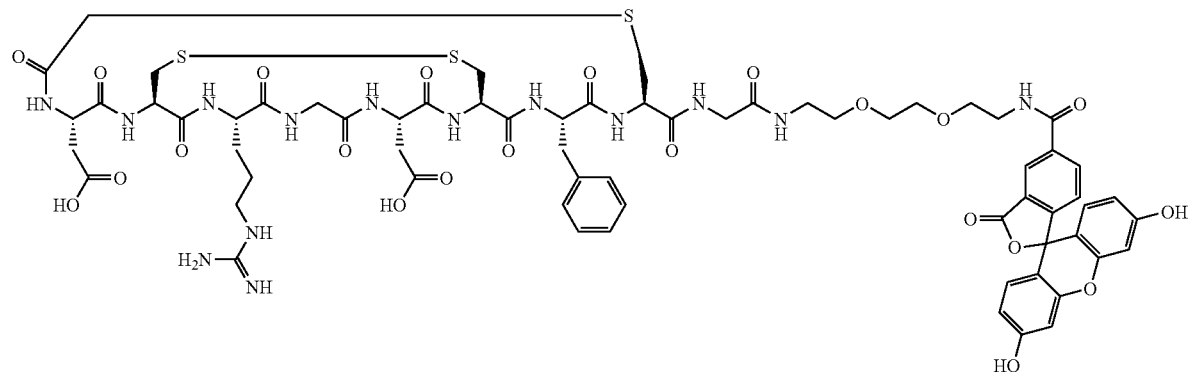

Other examples of compounds of the invention are illustrated by compounds C and D below.

Compound C:
The compound comprises an RGD peptide (Lys-Asp-Cys-Arg-Gly-Asp-Cys-Phe-Cys-Gly) linked to fluorescein, forming a "discrete" configuration.

Compound D:
The compound comprises an RGD-peptide (Lys-Cys-Arg-Gly-Asp-Cys-Phe-Cys) linked to fluorescein, forming an "interlocking" configuration.

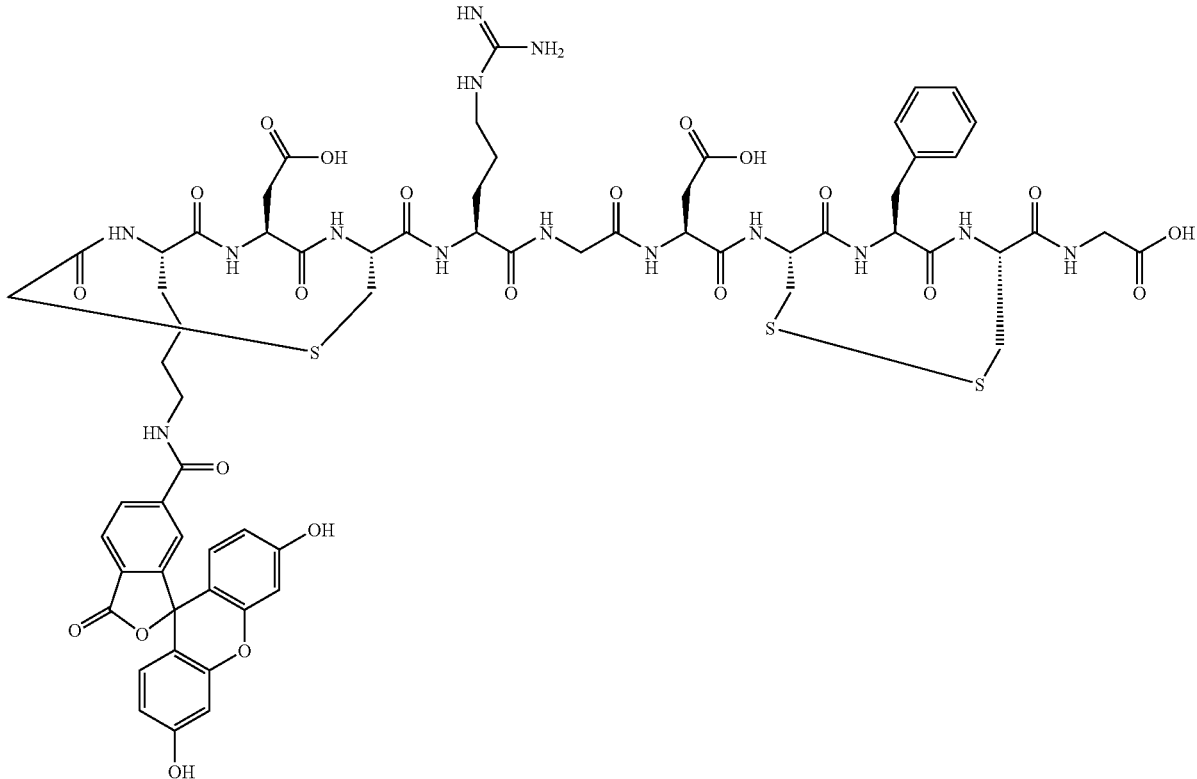

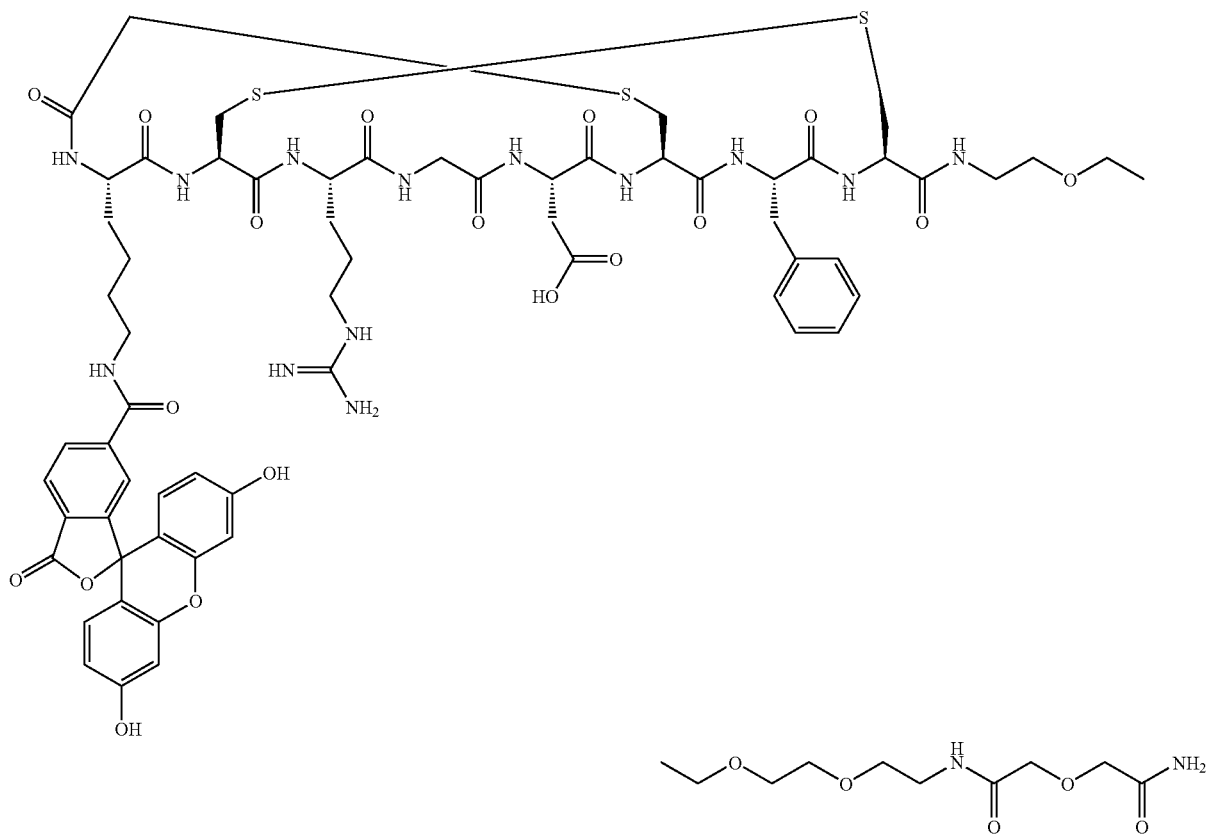

The new compounds of the invention may be used as contrast agents in optical imaging or for treatment of diseases. Use of the compounds as described for treatment or as contrast agents in optical imaging is hence an embodiment of the invention. A preferred embodiment of the invention is compounds as described for use as optical imaging contrast agent, particularly for use in optical imaging of and diagnosing of angiogenesis-related diseases.

The compounds of this invention are useful as imaging agents in the detection of angiogenesis in both humans and animals. The products may also have utility in pre-clinical animal models and allow monitoring of therapeutic efficacy of new drugs within pharmaceutical research, e.g. in oncology.

The present invention also provides a pharmaceutical composition comprising an effective amount, e.g. an amount effective for enhancing image contrast in in vivo imaging of a compound of the invention, or a salt thereof, together with one or more pharmaceutically acceptable adjuvants, excipients or diluents.

The invention further provides a pharmaceutical composition for treatment of a disease comprising an effective amount of a compound of the invention, or a salt thereof, together with one or more pharmaceutically acceptable adjuvants, excipients or diluents.

Viewed from a further aspect the invention provides the use of a compound of the invention for the manufacture of an optical imaging contrast medium for use in a method of diagnosis involving administration of said contrast medium to a human or animal body and generation of an image of at least part of said body.

Use of the compounds in the manufacture of therapeutic compositions (medicament) and in methods of therapeutic or prophylactic treatment, preferably treatment of angiogenesis-related diseases, of the human or animal body are thus considered to represent further aspects of the invention.

Viewed from a still further aspect the invention provides a method of generating an image of a human or animal body by optical imaging involving administering a contrast agent to said body, e.g. into the vascular system and generating an image of at least a part of said body, to which said contrast agent has distributed, wherein as said contrast agent is used a compound as described.

Viewed from a still further aspect the invention provides a method of generating enhanced images of a human or animal body by optical imaging previously administered with a contrast agent composition comprising a compound as defined, which method comprises generating an image of at least part of said body.

Viewed from a further aspect the invention provides a method of monitoring the effect of treatment of a human or animal body with a drug to combat a condition associated with angiogenesis, said method involving administering to said body an agent of the invention and detecting the uptake of said agent by cell receptors, preferably endothelial cell receptors and in particular αvβ3 receptors, said administration and detection optionally but preferably being effected repeatedly, e.g. before, during and after treatment with said drug. Said detection comprising an optical imaging technique.

Since fluorescein as well as the fluorescein-peptide compound of the present invention emits in the visual range of the spectrum, conventional ophthalmoscopy equipment may be used for acquiring the images. Furthermore, in-vivo confocal microscopy may be applied. Recently developed time-domain and frequency-domain imaging techniques may potentially also be used, taking advantage of additional characteristics of the fluorophore, such as lifetime.

The compounds of the present invention can be synthesized using all the known methods of chemical synthesis but particularly useful is the solid-phase methodology of Merrifield employing an automated peptide synthesizer (J. Am. Chem. Soc., 85: 2149 (1964)). In addition, coupling of fluorescein, such as a fluorescein active ester, can also be carried out automatically yielding an amide bond between the peptitic vector and the fluorescein group. The peptidic vector and the peptide compound may be purified using high performance liquid chromatography (HPLC) and characterized by mass spectrometry and analytical HPLC before testing in the in vitro screen.

The present invention will now be further illustrated by way of the following non-limiting examples.

EXAMPLES

Example 1

Synthesis of Disulphide [$Cys^{2-6}$] Thioether Cyclo [$CH_2CO$-Lys(fluorescein)-$Cys^2$-Arg-Gly-Asp-$Cys^6$-Phe-Cys]-PEG-$NH_2$ 1 a) Synthesis of 17-(Fmoc-amino)-5-oxo-6-aza-3,9, 12,15-tetraoxaheptadecanoic Acid

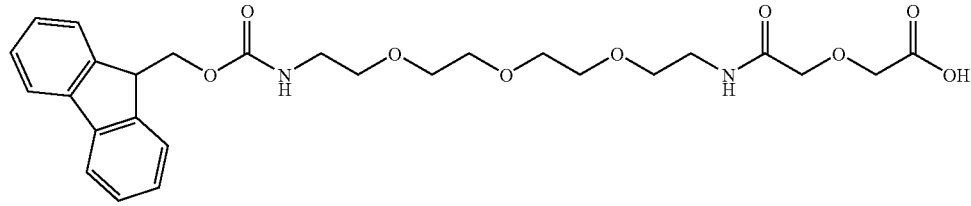

This building block is coupled to the solid-phase using Fmoc chemistry. The coupled form of this building block will be referred to in short as PEG.

1,11-Diazido-3,6,9-trioxaundecane

A solution of dry tetraethylene glycol (19.4 g, 0.100 mol) and methanesulphonyl chloride (25.2 g, 0.220 mol) in dry THF (100 ml) was kept under argon and cooled to 0° C. in an ice/water bath. To the flask was added a solution of triethylamine (22.6 g, 0.220 mol) in dry THF (25 ml) dropwise over 45 min. After 1 hr the cooling bath was removed and stirring was continued for 4 hrs. Water (60 ml) was added. To the mixture was added sodium hydrogencarbonate (6 g, to pH 8) and sodium azide (14.3 g, 0.220 mmol), in that order. THF was removed by distillation and the aqueous solution was refluxed for 24 h (two layers formed). The mixture was cooled and ether (100 ml) was added. The aqueous phase was saturated with sodium chloride. The phases were separated and the aqueous phase was extracted with ether (4×50 ml).

Combined organic phases were washed with brine (2×50 ml) and dried ($MgSO_4$). Filtration and concentration gave 22.1 g (91%) of yellow oil. The product was used in the next step without further purification.

11-Azido-3,6,9-trioxaundecanamine

To a mechanically, vigorously stirred suspension of 1,11-diazido-3,6,9-trioxaundecane (20.8 g, 0.085 mol) in 5% hydrochloric acid (200 ml) was added a solution of triphenylphosphine (19.9 g, 0.073 mol) in ether (150 ml) over 3 hrs at room temperature. The reaction mixture was stirred for additional 24 hrs. The phases were separated and the aqueous phase was extracted with dichloromethane (3×40 ml). The aqueous phase was cooled in an ice/water bath and pH was adjusted to ca 12 by addition of KOH. The product was extracted into dichloromethane (5×50 ml). Combined organic phases were dried ($MgSO_4$). Filtration and evaporation gave 14.0 g (88%) of yellow oil. Analysis by MALDI-TOF mass spectroscopy (matrix: α-cyano-4-hydroxycinnamic acid) gave a M+H peak at 219 as expected. Further characterisation using $^1H$ (500 MHz) and $^{13}C$ (125 MHz) NMR spectroscopy verified the structure.

17-Azido-5-oxo-6-aza-3,9,12,15-tetraoxaheptadecanoic Acid

To a solution of 11-azido-3,6,9-trioxaundecanamine (10.9 g, 50.0 mmol) in dichloromethane (100 ml) was added diglycolic anhydride (6.38 g, 55.0 mmol). The reaction mixture was stirred overnight. HPLC analysis (column Vydac 218TP54; solvents: A=water/0.1% TFA and B=acetonitrile/ 0.1% TFA; gradient 4-16% B over 20 min; flow 1.0 ml/min; UV detection at 214 and 284 nm), showed complete conversion of starting material to a product with retention time 18.3 min. The solution was concentrated to give quantitative yield of a yellow syrup. The product was analysed by LC-MS (ES ionisation) giving [MH]+at 335 as expected. $^1H$ (500 MHz) and $^{13}C$ (125 MHz) NMR spectroscopy was in agreement with structure The product was used in the next step without further purification.

17-Amino-5-oxo-6-aza-3,9,12,15-tetraoxaheptadecanoic Acid

A solution of 17-azido-5-oxo-6-aza-3,9,12,15-tetraoxaheptadecanoic acid (8.36 g, 25.0 mmol) in water (100 ml) was reduced using $H_2$ (g)-Pd/C (10%). The reaction was run until LC-MS analysis showed complete conversion of starting material (column Vydac 218TP54; solvents: A=water/0.1% TFA and B=acetonitrile/0.1% TFA; gradient 4-16% B over 20 min; flow 1.0 ml/min; UV detection at 214 and 284 nm, ES ionisation giving M+H at 335 for starting material and 309 for the product). The solution was filtered and used directly in the next step.

17-(Fmoc-amino)-5-oxo-6-aza-3,9,12,15-tetraoxa-heptadecanoic Acid

To the aqueous solution of 17-amino-5-oxo-6-aza-3,9,12,15-tetraoxaheptadecanoic acid from above (corresponding to 25.0 mmol amino acid) was added sodium bicarbonate (5.04 g, 60.0 mmol) and dioxan (40 ml). A solution of Fmoc-chloride (7.11 g, 0.275 mol) in dioxan (40 ml) was added dropwise. The reaction mixture was stirred overnight. Dioxan was evaporated off (rotavapor) and the aqueous phase was extracted with ethyl acetate. The aqueous phase was acidified by addition of hydrochloric acid and precipitated material was extracted into chloroform. The organic phase was dried ($MgSO_4$), filtered and concentrated to give 11.3 g (85%) of a yellow syrup. The structure was confirmed by LC-MS analysis (column Vydac 218TP54; solvents: A=water/0.1% TFA and B=acetonitrile/0.1% TFA; gradient 40-60% B over 20 min; flow 1.0 ml/min; UV detection at 214 and 254 nm, ES ionisation giving M+H at 531 as expected for the product peak at 5, 8 minutes). The analysis showed very low content of side products and the material was used without further purification.

1 b) Synthesis of $ClCH_2CO$-Lys-Cys(tBu)-Arg-Gly-Asp-Cys(tBu)-Phe-Cys-PEG-$NH_2$ The PEG unit was coupled manually to Rink Amide AM resin, starting on a 0.25 mmol scale, mediated by HATU activation. The remaining peptide was assembled on an ABI 433A automatic peptide synthesiser using 1 mmol amino acid cartridges. The amino acids were pre-activated using HBTU before coupling. N-terminal amine, groups were chloroacetylated using a solution of chloroacetic anhydride in DMF for 30 min. The simultaneous removal of peptide and side-chain protecting groups (except tBu) from the resin was carried out in TFA containing TIS (5%), $H_2O$ (5%) and phenol (2.5%) for two hours. After work-up 322 mg of crude peptide was obtained (Analytical HPLC: Gradient, 5-50% B over 10 min where A=$H_2O$/0.1% TFA and B=$CH_3CN$/0.1% TFA; column, Phenomenex Luna 3μC18 (2) 50×4.6 mm; flow, 2 mL/min; detection, UV 214 nm; product retention time, 6.37 min). Further product characterisation was carried out using mass spectrometry: Expected, M+H at 1409, found, at 1415).

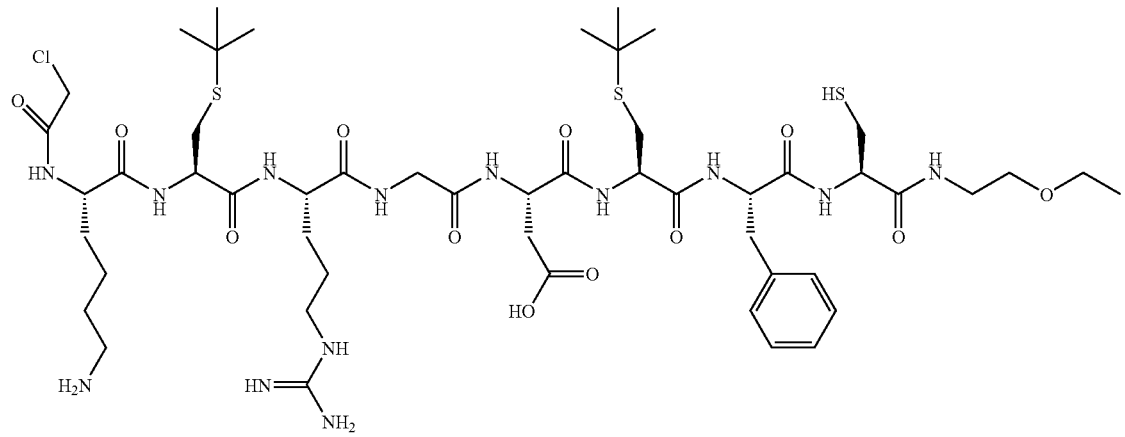

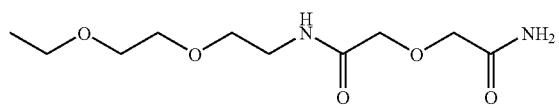

Molecular Weight = 1409.163
Exact Mass = 1407.612
Molecular Formula = C58H98ClN15O17S3

1 c) Synthesis of Thioether Cyclo[CH₂CO-Lys-Cys (tBu)-Arg-Gly-Asp-Cys(tBu)-Phe-Cys]-PEG-NH₂

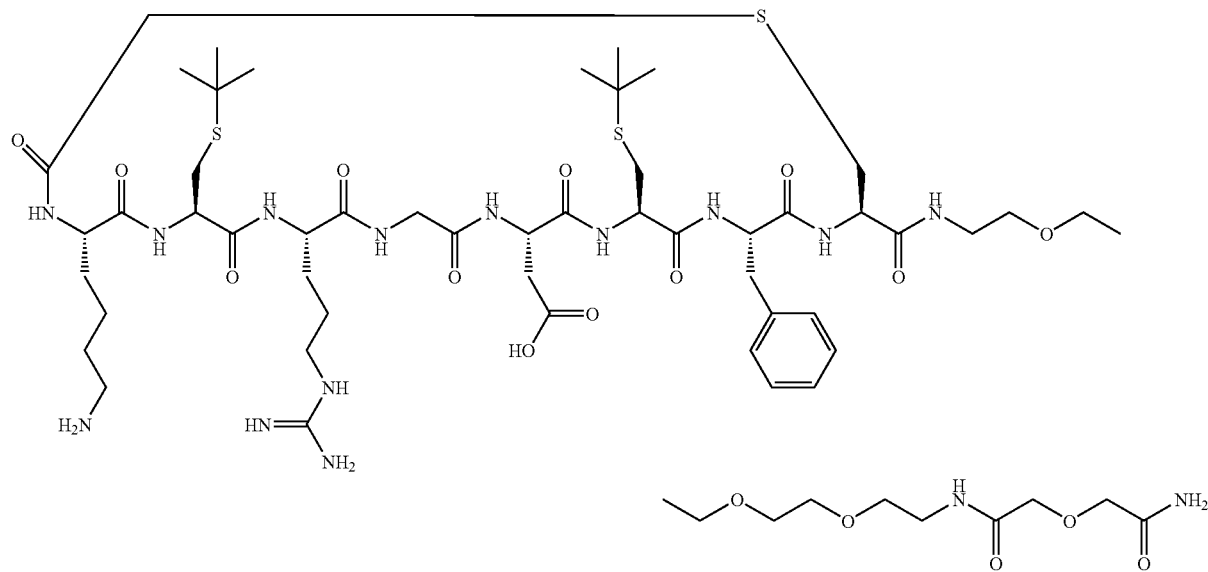

Molecular Weight = 1372.702
Exact Mass = 1371.635
Molecular Formula = C58H97N15O17S3

322 mg of ClCH₂CO-Lys-Cys (tBu)-Arg-Gly-Asp-Cys (tBu)-Phe-Cys-(PEG)n-NH₂ was dissolved in water/acetonitrile. The mixture was adjusted to pH 8 with ammonia solution and stirred for 16 hours. After work-up crude peptide was obtained (Analytical HPLC: Gradient, 5-50% B over 10 min where A=H₂O/0.1% TFA and B=CH₃CN/0.1% TFA; column, Phenomenex Luna 3 μC18 (2) 50×4.6 mm; flow, 2 mL/min; detection, UV 214 nm; product retention time, 6.22 min). Further product characterisation was carried out using mass spectrometry: Expected, M+H at 1373, found, at 1378).

1 d) Synthesis of Disulphide[Cys$^{2-6}$] Thioether Cyclo[CH₂CO-Lys-Cys$^2$-Arg-Gly-Asp-Cys $^6$-Phe-Cys]-PEG-NH₂

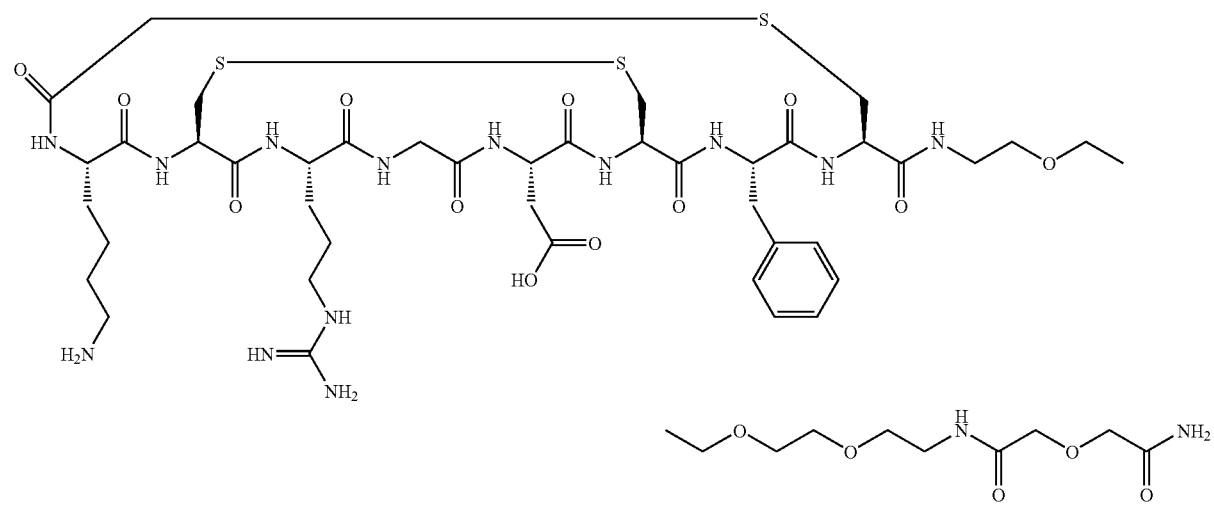

Molecular Weight = 1258.469
Exact Mass = 1257.494
Molecular Formula = C50H79N15O17S3

Thioether cyclo[CH₂CO-Lys-Cys (tBu)-Arg-Gly-Asp-Cys (tBu)-Phe-Cys]-(PEG)n-NH₂ was treated with a solution of anisole (200 μL), DMSO (2 mL) and TFA (100 mL) for 60 min following which the TFA was removed in vacuo and the peptide precipitated by the addition of diethyl ether. Purification by preparative HPLC (Phenomenex Luna 5μ C18 (2) 250×21.20 mm column) of 70 mg crude material was carried out using 0-30% B, where A=H₂O/0.1% TFA and B=CH₃CN/0.1% TFA, over 40 min at a flow rate of 10 mL/min. After lyophilisation 46 mg of pure material was obtained (Analytical HPLC: Gradient, 0-30% B over 10 min where A=H₂O/0.1% TFA and B=CH₃CN/0.1% TFA; column, Phenomenex Luna 3μ C18 (2) 50×4.6 mm; flow, 2 mL/min; detection, UV 214 nm; product retention time, 6.80 min). Further product characterisation was carried out using mass spectrometry: Expected, M+H at 1258.5, found, at 1258.8).

1 e) Synthesis of Disulfide [Cys$^{2-6}$] Thioether cyclo [CH₂CO-Lys(fluorescein)-Cys$^2$-Arg-Gly-Asp-Cys$^6$-Phe-Cys]-PEG-NH₂

30 mg of [Cys $^{2-6}$] cyclo[CH₂CO-Lys-Cys-Arg-Gly-Asp-Cys-Phe-Cys]-PEG-N₂, 16.2 mg of Fluorescein NHS ester and 4 μL of N-methylmorpholine was dissolved in DMF (3 mL). The mixture was protected against light and stirred over night. Purification by preparative HPLC (Vydac 218TP1022 C18 column) of the reaction mixture was carried out using 20-30% B, where A=H₂O/0.1% TFA and B=CH₃CN/0.1% TFA, over 40 min at a flow rate of 10 mL/min. After lyophilisation 21.6 mg of pure material was obtained (Analytical HPLC: Gradient, 10-40% B over 10 min where A=H₂O/0.1% TFA and B=CH₃CN/0.1% TFA; column, Phenomenex Luna 3μ C18 (2) 50×4.6 mm; flow, 2 mL/min; detection, UV 214 nm; product retention time, 7.0 min). Further product characterisation was carried out using mass spectrometry: Expected, M+H at 1616.5, found, at 1616.3).

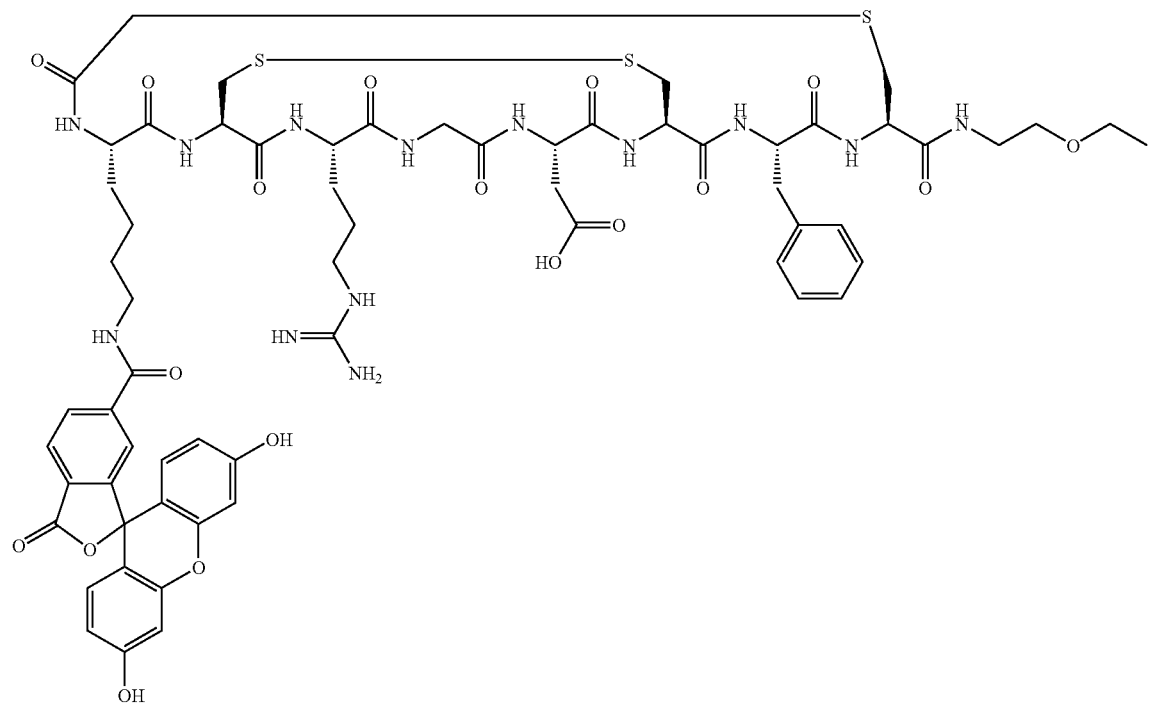

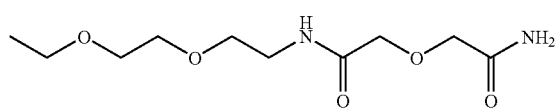

Molecular Weight = 1616.78
Exact Mass = 1615.54
Molecular Formula = C71H89N15O23S3

Example 2

Synthesis of Disulphide [Cys$^{2-6}$]thioether Cyclo [CH$_2$CO-Asp-Cys$^2$-Arg-Gly-Asp-Cys-Phe-Cys-Gly]-Bis(aminoethyl)ethylene glycol-fluorescein

2a. Synthesis of ClCH$_2$CONH-Asp-Cys (tBu)-Arg-Gly-Asp-Cys (tBu)-Phe-Cys-Gly-NH—(CH$_2$CH$_2$O)$_2$CH$_2$CH$_2$NH$_2$

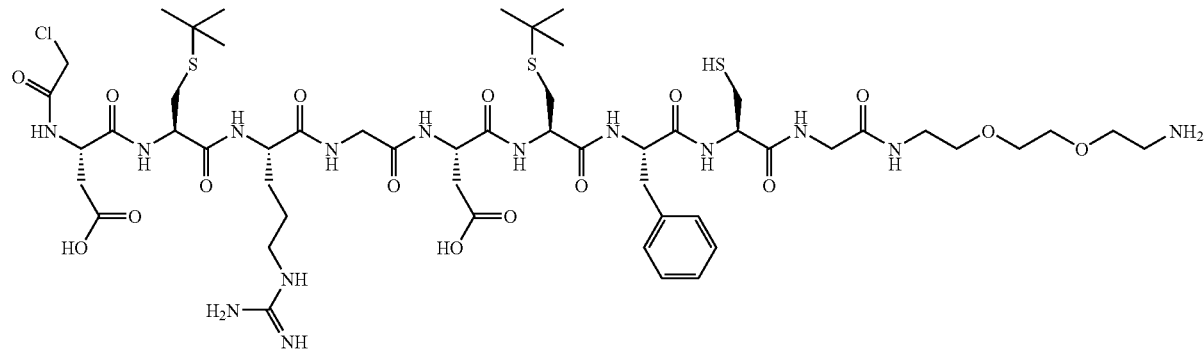

Molecular Weight = 1293.986
Exact Mass = 1292.512
Molecular Formula = C52H85ClN14O16S3

2b. Synthesis of Cyclo[CH$_2$CONH-Asp-Cys(tBu)-Arg-Gly-Asp-Cys (tBu)-Phe-Cys]-Gly-NH—(CH$_2$CH$_2$O)$_2$CH$_2$CH$_2$NH$_2$

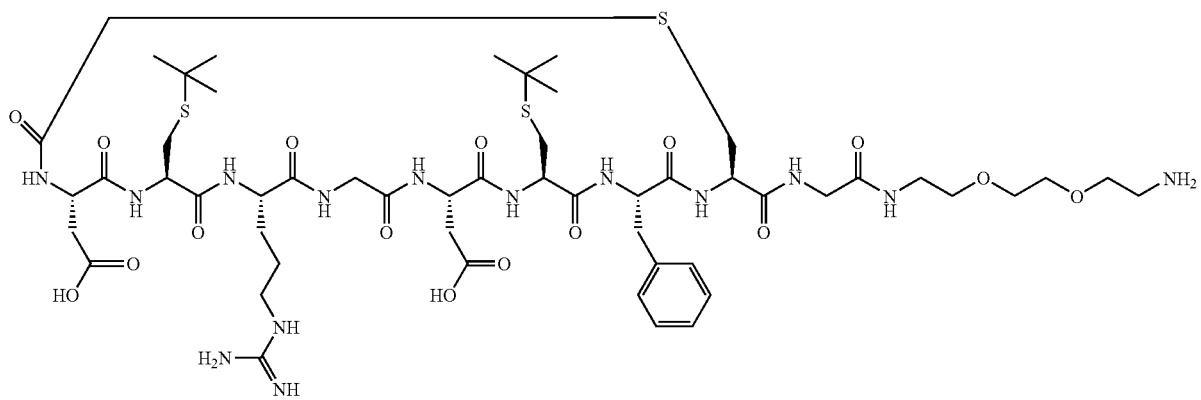

Molecular Weight = 1257.525
Exact Mass = 1256.535
Molecular Formula = C52H84N14O16S3

The peptide was synthesised on a ABI 433A automatic peptide synthesiser starting with O-Bis-(aminoethyl)ethylene glycol trityl resin on a 0.25 mmol scale using 1 mmol amino cartridges. The amino acids were pre-activated using HBTU before coupling. The N-terminal was chloroacetylated using chloroacetic anhydride. The simultaneous removal of peptide and side-chain protecting groups (except tBu) from the resin was carried out in TFA containing TIS (5%), H$_2$O (5%) and phenol (2.5%) for two hours. After work-up 364 mg of crude peptide was obtained (Analytical HPLC: Gradient, 5-50% B over 10 min where A=H$_2$O/0.1% TFA and B═CH$_3$CN/0.1% TFA; 2 mL/min; column, Phenomenex Luna 3μ C18 (2) 50×4.6 mm; detection, UV 214 nm; product retention time, 6.55 min). Further product characterisation was carried out using electrospray mass spectrometry: expected, M+H at 1293.5, found, at 1293.4).

250 mg of ClCH$_2$CONH-Asp-Cys (tBu)-Arg-Gly-Asp-Cys (tBu)-Phe-Cys-Gly-NH— (CH$_2$CH$_2$O)$_2$CH$_2$CH$_2$NH$_2$ was dissolved in water/acetonitrile. The mixture was adjusted to pH 8 with ammonia solution and stirred for 18 hours. After lyophilisation the crude peptide was obtained as a white powder. (Analytical HPLC: Gradient, 5-50% B over 10 min where A=H$_2$O/0.1% TFA and B═CH$_3$CN/0.1% TFA; flow, 2 mL/min; column, Phenomenex Luna 3μ C18 (2) 50×4.6 mm; detection, UV 214 nm; product retention time, 6.17 min).

Further product characterisation was carried out using electrospray mass spectrometry: expected, M+H at 1257.5, found, at 1257.6).

2c. Synthesis of [Cys$^{2-6}$] Cyclo[CH$_2$CONH-Asp-Cys-Arg-Gly-Asp-Cys-Phe-Cys]-Gly-NH—(CH$_2$CH$_2$O)$_2$CH$_2$CH$_2$NH$_2$ obtained. (Analytical HPLC: Gradient, 0-30% B over 10 min where A=H$_2$O/0.1% TFA and B=CH$_3$CN/0.1% TFA; flow, 2 mL/min; column, Phenomenex Luna 3µ C18 (2) 50×4.6 mm; detection, UV 214 nm; product retention time, 5.88 min). Further product characterization was carried out using electrospray mass spectrometry: expected, M+H at 1143.4, found, at 1143.5).

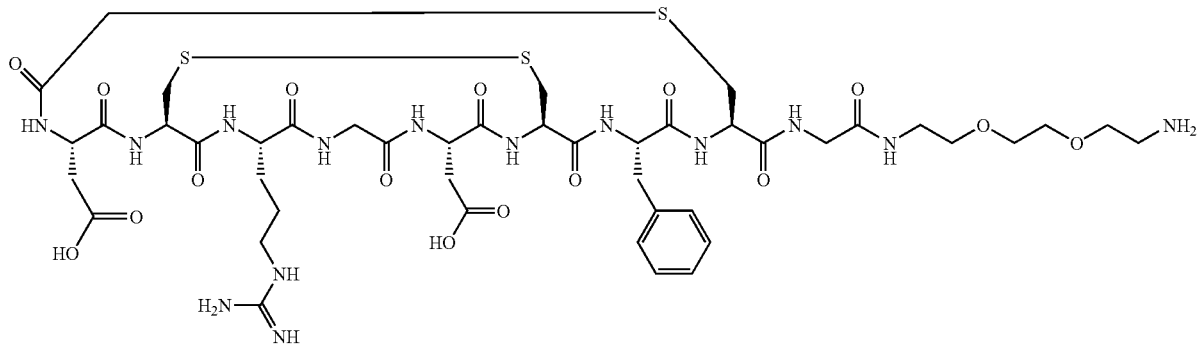

Molecular Weight = 1143.293
Exact Mass = 1142.394
Molecular Formula = C44H66N14O16S3

2d. Conjugation of [Cys$^{2-6}$] Cyclo[CH$_2$CONH-Asp-Cys-Arg-Gly-Asp-Cys-Phe-Cys]-Gly-NH—(CH$_2$CH$_2$O)$_2$CH$_2$CH$_2$NH$_2$ with Fluorescein

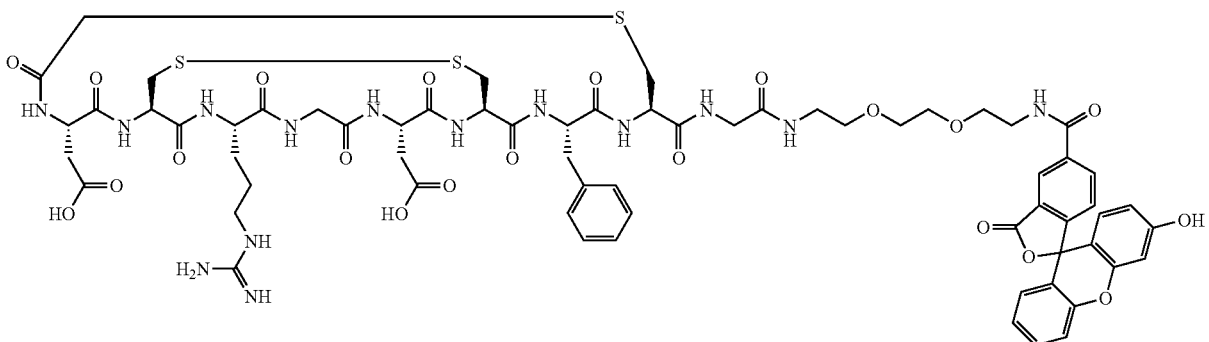

Molecular Weight = 1501.603
Exact Mass = 1500.442
Molecular Formula = C65H76N14O22S3

Cyclo [CH$_2$CONH-Asp-Cys (tBu)-Arg-Gly-Asp-Cys(tBu)-Phe-Cys]-Gly-NH—(CH$_2$CH$_2$O)$_2$CH$_2$CH$_2$NH$_2$ was dissolved in a solution of anisole (500 µl), DMSO (4 ml) and TFA (200 ml). The mixture was stirred at room temperature for 15 min following which the TFA was removed in vacuo and the peptide precipitated by the addition of diethyl ether. Purification by preparative HPLC (Phenomenex Luna 5µ C18 (2) 250×21.20 mm column) of the crude material was carried out using 0-30% B, where A=H$_2$O/0.1% TFA and B=CH$_3$CN/0.1% TFA, over 40 min at a flow rate of 10 mL/min. After lyophilisation 44 mg of pure material was obtained.

10 mg of [Cys$^{2-6}$] cyclo[CH$_2$CONH-Asp-Cys-Arg-Gly-Asp-Cys-Phe-Cys]-Gly-NH—(CH$_2$CH$_2$O)$_2$CH$_2$CH$_2$NH$_2$, 4.7 mg of fluorescein NHS ester and 5 µL of 4-methylmorpholine were dissolved in DMF (0.5 mL) and the solution stirred for 3 hours. Purification by preparative HPLC (Phenomenex Luna 5µ C18 (2) 250×21.20 mm column) of the crude material was carried out using 0-30% B, where A=H$_2$O/0.1% TFA and B=CH$_3$CN/0.1% TFA, over 40 min at a flow rate of 10 mL/min. After lyophilisation 6 mg of pure material was obtained. (Analytical HPLC: Gradient, 0-30% B over 10 min where A=H$_2$O/0.1% TFA and B=CH$_3$CN/0.1% TFA; flow, 2 mL/min; column, Phenomenex Luna 3µ C18 (2) 50×4.6 mm;

detection, UV 214 nm; product retention time, 10.07 min). Further product characterisation was carried out using electrospray mass spectrometry: expected, M+H at 1501.4, found, at 1501.4).

What is claimed is:

1. A compound comprising a peptidic vector and at least one fluorescein dye, wherein the peptidic vector and the fluorescein dye are coupled, and wherein said peptidic vector is defined by formula I:

$$R_a-C(=O)-X_1-X_2-X_3-G-D-X_4-X_5-X_6-X_7 \quad (I)$$

wherein Formula I comprises two cyclising bridges, and wherein $R_a$ represents —$(CH_2)_n$— or —$(CH_2)_n$—$C_6H_4$— forming a bridge to one of $X_2$, $X_4$ or $X_6$, wherein n represents a positive integer from 1 to 10, and $X_1$ represents a bond or 1, 2, 3, 4 or 5 amino acid residues, wherein one amino acid residue is optionally functionalised with a spacer moiety, or said amino acid residue possesses a functional side-chain chosen from an acid or amine group, $X_2$ is an amino acid residue forming a cyclising bridge to one of $R_a$, $X_4$ or $X_6$;

$X_3$ represents arginine or N-methylarginine,

G represents glycine,

D represents aspartic acid, $X_4$ is an amino acid residue forming a cyclising bridge to one of $R_a$, $X_2$ or $X_6$;

$X_5$ represents a hydrophobic amino acid, and $X_6$ represents an amino acid residue forming a cyclising bridge to either $R_a$, $X_2$ or $X_4$, and $X_7$ represents a spacer or biomodifier moiety or is absent, wherein said biomodifier comprises a monodisperse polyethylene glycol (PEG) building block comprising 1 to 10 units of said building block; and, wherein at least one of the fluorescein dye is linked to one or more of the groups $X_1$, $X_6$, or $X_7$ optionally via a spacer group.

2. A compound as claimed in claim 1 selected from one of the formulae;

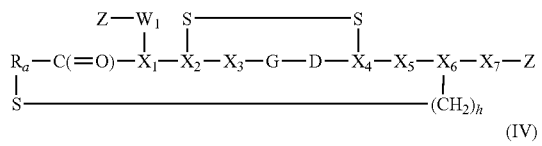

(III)

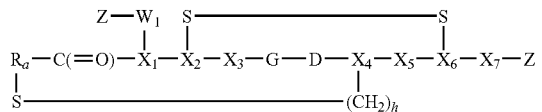

(IV)

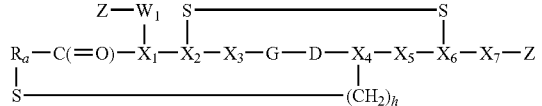

(V)

wherein $X_3$, G, and D are as defined in claim 1 and wherein $X_2$, $X_4$ and $X_6$ represent amino acid residues which together form a disulphide or a thioether bond as shown in Formulae III, IV or V, $W_1$ is a spacer moiety or is absent, h is a positive integer 1 or 2, and wherein Z represents a fluorescein dye.

3. A compound of formula III as claimed in claim 2 wherein $R_a$ represents —$(CH_2)$—.

4. A compound of formula III as claimed in claim 2 wherein $X_1$ represents an amino acid residue with a functional side-chain chosen from an acid or amine group, the amino acid being selected from aspartic acid, lysine, glutamic acid, homolysine or a diaminoalicylic acid.

5. A compound of formula III as claimed in claim 2 wherein $X_2$, $X_4$ and $X_6$ independently represent a cysteine or homocysteine residue.

6. A compound of formula III as claimed in claim 2 wherein $X_3$ represents arginine.

7. A compound of formula III as claimed in claim 2 wherein $X_5$ represents phenylalanine, tyrosine, a 3-iodo-tyrosine or naphthylalanine.

8. A pharmaceutical composition comprising an effective amount of a compound of claim 1, together with one or more pharmaceutically acceptable adjuvants, excipients or diluents.

9. An optical imaging contrast agent which comprises the compound of claim 1.

10. A method of generating images of a human or animal body by optical imaging involving administering the contrast agent of claim 9 to said body, and subsequently generating an image of at least a part of said body.

* * * * *

UNITED STATES PATENT AND TRADEMARK OFFICE
CERTIFICATE OF CORRECTION

PATENT NO. : 7,608,243 B2  Page 1 of 1
APPLICATION NO. : 10/560062
DATED : October 27, 2009
INVENTOR(S) : Cuthbertson et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 947 days.

Signed and Sealed this

Twelfth Day of October, 2010

David J. Kappos
*Director of the United States Patent and Trademark Office*